United States Patent
Mansfield et al.

(10) Patent No.: US 10,722,256 B2
(45) Date of Patent: Jul. 28, 2020

(54) STONE COLLECTION DEVICE

(71) Applicant: Gyrus ACMI, Inc., Southborough, MA (US)

(72) Inventors: Richard P. Mansfield, Sterling, MA (US); Michael J. Perriello, Hopedale, MA (US); Andy K. Khin, Lowell, MA (US)

(73) Assignee: Gyrus Acmi, Inc., Southborough, MA (US)

( * ) Notice: Subject to any disclaimer, the term of this patent is extended or adjusted under 35 U.S.C. 154(b) by 370 days.

(21) Appl. No.: 14/867,055

(22) Filed: Sep. 28, 2015

(65) Prior Publication Data

US 2017/0086861 A1   Mar. 30, 2017

(51) Int. Cl.
*A61B 17/22*   (2006.01)
*A61B 17/221*   (2006.01)

(52) U.S. Cl.
CPC .... *A61B 17/221* (2013.01); *A61B 2017/2212* (2013.01); *A61B 2017/2215* (2013.01)

(58) Field of Classification Search
CPC .......... A61B 17/22; A61B 17/221; A61B 17/3207–320758; A61B 17/22031–22032; A61B 17/32; A61B 17/320016–320036; A61B 2017/2212–2217;

(Continued)

(56) References Cited

U.S. PATENT DOCUMENTS

| | | |
|---|---|---|
| 7,875,038 B2 | 1/2011 | Que |
| 8,979,870 B2 | 3/2015 | Richardson |

(Continued)

FOREIGN PATENT DOCUMENTS

| | | |
|---|---|---|
| GB | 2418866 B | 9/2007 |
| WO | 00/053120 A1 | 9/2000 |
| WO | WO-2017058372 A1 | 4/2017 |

OTHER PUBLICATIONS

International Preliminary Report on Patentability for International Application No. PCT/US2016/047003, dated Apr. 3, 2018, 7 pages.

(Continued)

*Primary Examiner* — Vi X Nguyen
(74) *Attorney, Agent, or Firm* — Schwegman Lundberg & Woessner, P.A.

(57) ABSTRACT

Disclosed is a medical device comprising an outer elongate member having a proximal end, a distal end, and a lumen extending therethrough; an inner elongate member disposed within the lumen of the outer elongate member and configured to be axially movable inside the lumen of the outer elongate member, the inner elongate member having a proximal end portion, a distal end portion, and a lumen extending therethrough; an expandable cage-like scaffold having a proximal end secured to the distal end of the outer elongate member and a distal end having an inwardly everted tapering framework, the cage-like scaffold composed of a plurality of wires that cross each other at points, and capable of being actuated between a substantially folded configuration and a substantially open configuration. Also disclosed is a method of employing the above disclosed device or variations thereof to capture and remove stones or stone fragments from the body's lumen of a subject.

21 Claims, 6 Drawing Sheets

(58) Field of Classification Search
CPC ............... A61B 2017/320716–320775; A61B 2017/22001–22002; A61B 2017/22034–22049; A61B 2017/320004–320008; A61B 2017/320024–32004; A61B 17/32056; A61B 17/22012; A61B 17/22004; A61B 2017/2215; A61F 20/01–013; A61F 2002/011–018
See application file for complete search history.

(56) References Cited

U.S. PATENT DOCUMENTS

| | | | |
|---|---|---|---|
| 8,926,680 B2 | 6/2015 | Ferrera | |
| 2003/0195537 A1* | 10/2003 | Dubrul | A61B 17/221 606/159 |
| 2003/0212430 A1* | 11/2003 | Bose | A61B 17/221 606/200 |
| 2005/0070953 A1 | 3/2005 | Riley | |
| 2006/0058838 A1* | 3/2006 | Bose | A61B 17/22 606/200 |
| 2009/0299393 A1* | 12/2009 | Martin | A61B 17/221 606/159 |
| 2009/0306678 A1* | 12/2009 | Hardert | A61B 17/221 606/127 |
| 2012/0053596 A1 | 3/2012 | Gordon | |
| 2012/0059309 A1* | 3/2012 | di Palma | A61B 17/12186 604/22 |
| 2013/0131690 A1 | 5/2013 | Nagl | |
| 2013/0131703 A1 | 5/2013 | Fiorella | |
| 2014/0005717 A1 | 1/2014 | Martin | |
| 2014/0031855 A1 | 1/2014 | Clubb | |

OTHER PUBLICATIONS

"International Application Serial No. PCT/US2016/047003, International Search Report dated Nov. 18, 2016", 4 pgs.
"International Application Serial No. PCT/US2016/047003, Written Opinion dated Nov. 18, 2016", 6 pgs.

* cited by examiner

STONE COLLECTION DEVICE

FIELD

The embodiments of the present disclosure relate generally to a medical device and its related use for the capture and removal of unwanted solid materials from within the body's lumen of a subject. More particularly, the embodiments of the present disclosure relate to a medical device and its related use for the capture and removal of stone or stone fragments from within the body's lumen of a subject. Even more particularly, the embodiments of the present disclosure relate to a medical device and its related use for the capture and removal of stones or stone fragments from the ureter and/or kidney of a subject.

BACKGROUND

It is known that intracorporeal fragmentation of stones can under certain instances become problematic if the stones or stone fragments, instead of progressing out of the patient's body, begin to migrate further into the body or towards an organ. In these circumstances, further medical intervention to prevent aggravation of the patient's condition may become necessary. Therefore, it may be desirable to be able to extract such fragments from the body lumen using a single instrument, preventing the need for successive instrumentation which can cause greater trauma to the patient's tissue.

Many stone extraction devices such as stents, retrieval assemblies, and coiled medical extractions devices can be used to entrap solid materials such as stone fragments, and drag them out from within the body lumen to remove them. Coiled medical extraction devices may also be used to prevent unwanted migration of stone fragments generated during a stone fragmentation procedure, and then safely and efficiently extract fragments from the patient's body.

It is also known that current methods of breaking up kidney stones may result in large amounts of small stone fragments scattered in the ureter or kidney. Standard baskets struggle to grasp these small stone fragments, and these large amounts of stone fragments mean longer procedures if they are to be removed independently. Any stone fragments left behind after the completion of the procedure can become nucleation points for new stone formation or may be painful to pass naturally.

U.S. Pat. No. 6,800,080 describes a device for immobilization and/or retrieval of solid materials from a body. The disclosed device includes a sheath and a basket. The disclosed basket is movable relative to the sheath from a retracted position in which the basket is withdrawn within the sheath and an expanded position in which the basket is extended beyond the distal end of the sheath and open. The disclosed basket has a first portion and a second portion with two or more legs extending from the first portion to the second portion. The disclosed basket further includes an intermediate portion between the first and second portions in which the legs are spirally arranged, substantially parallel, and non-intersecting. The intermediate portion of the basket is displaced radially outward relative to the first and second portions when the basket is in the expanded position. The disclosed basket in the expanded position may be used to immobilize and/or capture solid materials within a body.

U.S. Pat. No. 8,979,870 discloses a device and related method of use for the capture and removal of various unwanted objects present within the body's anatomical lumens. The disclosed device includes an external elongate member; an internal elongate member disposed within the external elongate member; and a retrieval assembly connected to the internal elongate member and retractable within and extendable from a lumen of the external elongate member, wherein the retrieval assembly includes an end configured to be selectively open or substantially closed.

U.S. Pat. No. 8,926,680 discloses devices, methods and systems that facilitate and enable vessel wall treatment, particularly at the neck of an aneurysm. More particularly, it discloses a tethered cage-like structure that functions in conjunction with supplemental therapies such as a vaso-occlusive coil delivering microcatheter system and/or pharmaceutical delivery, among other things, by stabilizing vessel walls and providing tethered cage-like therapeutic support for treating aneurysms, temporarily or on an implantable basis.

U.S. patent application publication No. US2012/0/053, 596A1 discloses an apparatus having a longitudinal shaft having a guide feature and at least one ensnarement feature. The disclosed guide feature is disposed adjacent to a distal end of the longitudinal shaft, and the disclosed at least one ensnarement feature is disposed at least partially proximally relative to the guide feature.

U.S. patent application publication No. US2005/0,070, 953A1 discloses a device and related methods of use for the capture and removal of various unwanted objects present within the body's anatomical lumens. The disclosed device includes a sheath; an actuation handle; an end-effector loop connected to the actuation handle and retractable within and extendable from a lumen of the sheath; and a connecting member disposed within the sheath for deflecting the end-effector loop relative to the longitudinal axis of the device, wherein the end-effector loop includes an outer periphery that defines a space that may include a webbing.

SUMMARY

In an embodiment, the present disclosure provides a medical device comprising an outer elongate member having a proximal end, a distal end, and a lumen extending therethrough; an inner elongate member disposed within the lumen of the outer elongate member and configured to be axially movable relative to the outer elongate member, the inner elongate member having a proximal end portion, a distal end portion, and a lumen extending therethrough; and an expandable cage-like scaffold having a proximal end secured to the distal end of the outer elongate member and a distal end having an inwardly everted tapering framework, the cage-like scaffold composed of a plurality of wires that cross each other at points, and capable of being actuated between a substantially folded configuration and a substantially open configuration. In an embodiment, the medical device further comprises an actuator configured to actuate the expandable cage-like scaffold between the substantially folded configuration and the substantially open configuration. In an embodiment, the medical device further comprises an additional actuator configured to move the inner elongate member axially within the lumen of the outer elongate member. In an embodiment, the inwardly everted tapering framework comprises a head portion and a tail portion. In an embodiment, the distal end portion of the inner elongate member further comprises an opening.

In an embodiment, the present disclosure discloses a medical device comprising an outer elongate member having a proximal end, a distal end, and a lumen extending therethrough; an inner elongate member disposed within the lumen of the outer elongate member and configured to be axially movable relative to the outer elongate member, the inner elongate member having a proximal end portion, a distal end portion, and a lumen extending therethrough; and an expandable cage-like scaffold comprising a plurality of wires that cross each other at points, and capable of being actuated between a substantially folded configuration and a substantially open configuration, the cage-like scaffold having a proximal end and a distal end, wherein the proximal end of the cage-like scaffold is secured to the distal end of the outer elongate member and wherein the distal end has an inwardly everted tapering framework. In an embodiment, the medical device further comprises an actuator configured to actuate the expandable cage-like scaffold between the substantially folded configuration and the substantially open configuration. In an embodiment, the medical device further comprises an additional actuator configured to move the inner elongate member axially within the lumen of the outer elongate member. In an embodiment, the inwardly everted tapering framework comprises a head portion and a tail portion. In an embodiment, the distal end portion of the inner elongate member further comprises an opening.

In an embodiment, the present disclosure provides a method of capturing and removing solid materials from within the body lumen of a subject, the method comprising providing a medical device or variations thereof as described herein; inserting the medical device into a body lumen; and actuating the actuators of the medical device to capture and remove the solid materials from the body lumen of the subject.

DETAILED DESCRIPTION

Figure 1:
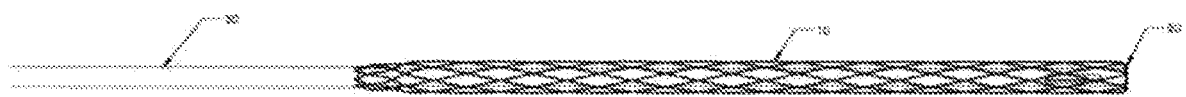
FIG. 1 is a schematic representation of a device or system in accordance with one embodiment of the present disclosure wherein the meshed scaffold is in collapsed configuration.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

The term "proximal" is herein used to mean a position or direction closest to a user of the device and is in a position or direction opposite to the term "distal".

The term "distal" is herein used to mean a position or direction furthest away from a user of the device and is a position or direction opposite to the term :proximal".

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value.

In an embodiment, the present disclosure provides a medical device comprising an outer elongate member having a proximal end, a distal end, and a lumen extending therethrough; an inner elongate member disposed within the lumen of the outer elongate member and configured to be axially movable relative to the outer elongate member, the inner elongate member having a proximal end portion, a distal end portion, and a lumen extending therethrough; and an expandable cage-like scaffold having a proximal end secured to the distal end of the outer elongate member and a distal end having an inwardly everted tapering framework, the cage-like scaffold composed of a plurality of wires that cross each other at points, and capable of being actuated between a substantially folded configuration and a substantially open configuration. In an embodiment, the medical device further comprises an actuator configured to actuate the expandable cage-like scaffold between the substantially folded configuration and the substantially open configuration. In an embodiment, the medical device further comprises an additional actuator configured to move the inner elongate member axially within and beyond the lumen of the outer elongate member. In an embodiment, the inwardly everted tapering framework comprises a head portion and a tail portion. In an embodiment, the distal end portion of the inner elongate member further comprises an opening.

In an embodiment, the present disclosure discloses a medical device comprising an outer elongate member having a proximal end, a distal end, and a lumen extending therethrough; an inner elongate member disposed within the lumen of the outer elongate member and configured to be axially movable relative to the outer elongate member, the inner elongate member having a proximal end portion, a distal end portion, and a lumen extending therethrough; and an expandable cage-like scaffold comprising a plurality of wires that cross each other at points, and capable of being actuated between a substantially folded configuration and a substantially open configuration, the cage-like scaffold having a proximal end and a distal end, wherein the proximal end of the cage-like scaffold is secured to the distal end of the outer elongate member and the distal end has an inwardly everted tapering framework. In an embodiment, the medical device further comprises an actuator configured to actuate the expandable cage-like scaffold between the substantially folded configuration and the substantially open configuration. In an embodiment, the medical device further comprises an additional actuator configured to move the inner elongate member axially within the lumen of the outer elongate member. In an embodiment, the inwardly everted tapering framework comprises a head portion and a tail portion. In an embodiment, the distal end portion of the inner elongate member further comprises an opening.

In an embodiment of the present disclosure, a medical device may include: an outer elongate member having a proximal end, a distal end, and a lumen extending longitudinally between the proximal end and the distal end; an inner elongate member disposed within the lumen of the outer elongate member and moveable within and beyond the lumen of the outer elongate member; and a cage-like scaffold comprising a distal end having an inwardly everted tapering framework, and being configured to connect to the distal end of the outer elongate member, wherein the cage-like scaffold is configured to be capable of being actuated between a substantially folded configuration and a substantially open configuration. In an embodiment, the medical device further comprises an actuator configured to actuate the expandable cage-like scaffold between the substantially folded configuration and the substantially open configuration. In an embodiment, the medical device further comprises an additional actuator configured to move the inner elongate member axially within and beyond the lumen of the outer elongate member. In an embodiment, the inwardly everted tapering framework comprises a head portion and a tail portion. In an embodiment, the distal end portion of the inner elongate member further comprises an opening.

In the above embodiments, the outer elongate member may be made from any suitable flexible material such as plastic and by any known process such as extrusion. The outer elongate member may have any desirable cross-sectional shape and/or configuration, preferably substantially circular cross-section. The outer elongate member may also have one or more cross-sectional shapes and/or configurations along its length, and may have any desirable dimension suitable for deployment within a targeted body lumen such as a ureter. The overall length and diameter of the outer elongate member may vary in accordance with its intended application. A relatively long outer elongate member may be advantageous for retrieving solid materials or stones deep inside the body of a subject. The outer elongate member may be made to be flexible along at least portion of its length so that it may bend as it is advanced through a tortuous body lumen. The outer elongate member may have an outer diameter of less than 0.10 inch but larger than 0.01 inch. The outer elongate member may have an outer diameter of less than 0.06 inch but larger than 0.02 inch. The outer elongate member may have an outer diameter of about 0.044 inch.

In the above embodiments, the outer elongate member may be configured to be actuated or manipulated by the hand of a user through a handle at the proximal end of the outer elongate member. The handle may include one or more steering controls that may be actuated to steer the distal end of the outer elongate member. For example, it may be coupled to a pullwire to steer or control the distal end of the outer elongate member. It may also be configured to be actuated by other mechanism coupled to or otherwise provided on the proximal end of the outer elongate member. It may also be configured to be actuated or manipulated by any other control mechanism known in the art.

In the above embodiments, the lumen extending through the outer elongate member has a diameter that is slightly smaller than that of the outer elongate member. For example, it may have a diameter of less than 0.08 inch but larger than 0.01 inch, for example, about 0.06 inch, about 0.04 inch, or about 0.02 inch. In any event, it should have a diameter large enough to house the inner elongate member.

In the above embodiments, the inner elongate member may be configured to be extendable along the longitudinal direction through the lumen of the outer elongate member. It may be extendable beyond the lumen of the outer elongate member. It may be configured to be extendable beyond the distal end of the cage-like scaffold. The inner elongate member may be made from any suitable flexible material such as plastic and by any known process such as extrusion. The inner elongate member may have any desirable cross-sectional shape and/or configuration, preferably substantially circular cross-section. The inner elongate member may also have one or more cross-sectional shapes and/or configurations along its length. The overall length and diameter of the inner elongate member may vary in accordance with its intended application. A relatively long inner elongate member may advantageous for retrieving stones deep inside the body of a subject. The inner elongate member should have a diameter less than that of the outer elongate member. For example, it may have an outer diameter of less than 0.06 inch. It may have an outer diameter less than 0.04 inch. The inner elongate member should be made to be flexible along at least portion of its length so that it may bend as it is advanced through a tortuous body lumen. The inner elongate member may be further configured to have an opening at the distal end for directional flow and/or venting when the device is used for vacuum suction. The dimension and/or size and or location of the opening may vary based on different purposes. For example, the opening may have a dimension of about 0.10 inch in length and about 0.02 inch in width and may be disposed at a distance of between about 0.10 inch and about 0.20 inch from the end of the inner elongate member.

In the above embodiments, the inner elongate member may be configured to be actuated or manipulated in ways that are known in the art. For example, the inner elongate member may be configured to be actuated or manipulated by a handle at the proximal end of the inner elongate member. The handle may include one or more steering controls that may be actuated to steer the distal end portion of the inner elongate member. It may be coupled to a pullwire to steer or control the distal end portion of the inner elongate member. It may be configured to be actuated by other mechanism coupled to or otherwise provided on the proximal end portion of the inner elongate member. It may also be configured to be actuated through a guidewire receivable into the lumen of the inner elongate member. It may also be configured to be actuated or manipulated by any other control mechanism known in the art.

In the above embodiments, the cage-like scaffold may be made of any material suitable for self-expansion. These materials may be one or more metals and/or their composites such as, but not limited to, stainless steel or nitinol. The cage-like scaffold may be configured to have any suitable shape, for example, a cylindrical structure. The cage-like scaffold may be configured to have any desirable cross-sectional shape and/or configuration, preferably substantially circular cross-section. The overall length and diameter of the cage-like scaffold may vary in accordance with its intended application. The cage-like scaffold should have a configuration, dimensions or material properties that allow its longitudinal movement within an external access sheath for extension and/or retraction into and out of the external access sheath.

In the above embodiments, the plurality of wires of the cage-like scaffold may be configured to have any desirable pattern, configuration, and features that are suitable for entrapment of solid materials within a body lumen. The plurality of wires is woven to form or define series of cells or spaces. The plurality of wires may not be physically connected into each other. That is the wires may not be connected at crossing points. These cells or spaces may be configured to be of any suitable shape, size, and/or configuration. They may be, for example, in the shape of triangle, diamond, parallelogram, rectangle, square, other polygons, or other suitable geographic shape. The diameter of these cells or spaces may be in a range of between about 0.05 inch and about 0.15 inch.

In the above embodiments, the proximal end of the cage-like scaffold may be secured to the distal end of the outer elongate member through any suitable connections means. For example, the connection may be accomplished to fixedly connect the proximal end of the cage-like scaffold to the distal end of the outer elongate member by welding, soldering, and/or crimping. The proximal end of the cage-like scaffold may also be secured to the distal end of the outer elongate member by detachable mechanism well known in the art, for example, a snap mechanism that allows the proximal end of the cage-like scaffold snaps into the distal end of the outer elongate member. It may also be secured by other mechanisms known in the art.

In the above embodiments, the inwardly everted tapering framework of the cage-like scaffold comprises a head portion and a tail portion. The head portion starts from the ending part of the distal end of the cage-like scaffold and tapers inwardly to form the tail portion of the tapering framework. In an embodiment, the head portion may be in any suitable cross sectional shape such as a substantially circular shape. In an embodiment, the head portion may be configured to have a diameter of less than 0.40 inch but larger than 0.10 inch. In an embodiment, the tail portion may be in any suitable shape or configuration such as triangle, diamond, parallelogram, rectangle, square, polygons, or other suitable geographic shapes. The diameter of the tail portion may be in the range of less than 0.20 inch but larger than 0.02 inch. The longitudinal length of the inwardly everted tapering framework may be configured to be between about 10% and about 25% of the whole length of the cage-like scaffold as measured from the proximal end of the cage-like scaffold to the distal end of the cage-like scaffold. The tail portion may be configured to have an even ending, meaning all the ends of the wires end on the same plane substantially perpendicular to the longitudinal axis of the cage-like scaffold. In alternative terms, the tail portion may be configured to have substantially the same wire length extending from the head portion. The tail portion may be configured to have an uneven ending, meaning all the ends of the wires do not end on the same plane. In alternative terms, the tail portion may be configured to have substantially different wire length extending from the head portion. The uneven ends may be symmetrical or non-symmetrical with respect to the longitudinal axis. In alternative terms, the tail portion may be configured to have uneven wire endings.

In the above embodiments, the cage-like scaffold may further comprise an external sheath wherein the external sheath is used to keep the cage-like scaffold in its initial collapsed or folded configuration. The external sheath may be configured to be extendable to the proximal end of the outer elongate member for easy/convenient manipulation by a user. Similarly, the external sheath may be made from any suitable flexible material such as plastic and by any known process such as extrusion. The external sheath may be kept in place until or unless the cage-like scaffold or the medical device is inserted into an external access port. This type of process or procedure is well known in the art.

In the above embodiments, the medical device may be made reusable or disposable. In the above embodiments, the medical device may be preferably made disposable.

In an embodiment, the present disclosure provides a method of capturing and removing solid materials or stones from within the body of a subject, the method comprising providing a medical device or variations thereof as described herein; inserting the medical device into a body lumen; and actuating the actuators of the device to capture and remove the solid materials or stones from the body lumen of the subject.

In an embodiment, the present disclosure provides a method of capturing and removing solid materials from within the body of a subject. The method including inserting a medical device or variations thereof as described herein into a body lumen; advancing the medical device to a desired body location, actuating the cage-like scaffold to a substantially open configuration; capturing solid materials or stones within the cage-like scaffold; and removing the medical device and captured solid materials or stones from within the body.

In an embodiment, the method includes one or more of the following aspects: the outer elongate member may be retrieved proximally to deploy the cage-like scaffold within a body lumen. In an embodiment, the method may comprise the step of actuating the actuator to substantially close the cage-like scaffold. In an embodiment, the method may comprise the step of actuating the actuator to substantially open the cage-like scaffold. In an embodiment, the step of actuating the actuator to substantially open the cage-like scaffold may be performed after the cage-like scaffold is deployed within a body lumen. In an embodiment, the step of actuating the actuator to substantially close the cage-like scaffold may be performed prior to removing the medical device from within a body. In an embodiment, the method may further comprise releasing the solid materials from the cage-like scaffold after the device is taken out of the body lumen.

In an embodiment, the medical device described herein may be used in lithotripsy or ureteroscopy to treat kidney stones in the body of a patient. Lithotripsy is a medical procedure that uses energy in various forms such as acoustic shock waves, pneumatic pulsation, electro-hydraulic shock waves, or laser beams, to pulverize urinary calculi such as kidney stones. The force of the energy, when applied either extracorporeally or intracorporeally, breaks the stones down into smaller fragments that may be extracted from the body, or allowed to pass from the body, for example, through urination. In an embodiment, the solid materials to be removed are not limited to just kidney stones. They may include gallbladder stones, uric acid stones, or other materials.

In an embodiment, the present disclosure provides methods of using the medical device described herein to retrieve stones or other solid materials located in the bladder, ureter, kidney, or other body organs. The medical device may be inserted through the urethra of a subject, or percutaneously. The medical device may be used in any location of the body in which a passageway or orifice has unwanted solid materials to be removed.

In an embodiment, the medical device may be advanced to a treatment site through various ways. For example, the medical device may be advanced to a targeted location over a guidewire. In an embodiment, the medical device may be advanced to the targeted location by means of an imaging device. The medical device may also be advanced to the treatment site through an access sheath or any other suitable means known in the art.

In an embodiment, the medical device may be used in conjunction with an endoscope or any other type of intrcorporeal device known in the art. The endoscope may be inserted through a body lumen into a treatment site in any conventional manner. Once the endoscope is properly positioned adjacent to the treatment site, the medical device may be led through an access port of the endoscope to get access to the targeted region for capture and removal of stones.

It will be apparent to the skilled addressee that many modifications, variants and improvements are possible within the ambit of the invention defined herein. For example, a device in accordance with some embodiments as described may be employed during the extracorporeal procedure.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

FIG. 1 illustrates a medical device in accordance with one aspect of the present disclosure wherein the scaffold of the medical device is in a collapsed configuration. The medical device of FIG. 1 includes an outer elongate member 30, a self-expandable scaffold 10 having a proximal end secured to the distal end of the outer elongate member and a distal end 20, and an inner elongate member 40 disposed and movable within the lumen of the outer elongate member.

The outer elongate member 30 may be made of any suitable flexible material such as plastic and by any known process such as extrusion. The outer elongate member 30 may have any desirable cross-sectional shape and/or configuration. For example, it may be a tubular member with preferably substantially circular cross-section. A relatively long and flexible outer elongate member may be advantageous for retrieving stones deep inside the body of a subject.

The inner elongate member 40 may be made of any suitable flexible material such as plastic and by any known process such as extrusion. The inner elongate member 40 may have any desirable cross-sectional shape and/or configuration, preferably substantially circular cross-section. For example, it may be a tubular member with preferably substantially circular cross-section. A relatively long and flexible outer elongate member may be advantageous for retrieving stones deep inside the body of a subject.

The scaffold 10, a self-expandable meshed structure, is in its collapsed configuration. The scaffold 10 may be made of any material suitable for self-expansion. These materials may be one or more metals and/or their composites such as, but not limited to, stainless steel or nitinol. The scaffold 10 may be secured to the outer elongate member 30 by molding. It may also be attached to the distal end of the outer elongate member in a locking feature. It may also be attached to the distal end of the outer elongate member by a snap mechanism. The scaffold 10 may be maintained in its initial collapsed configuration by an external sheath (not shown). Once the medical device is inserted into an access port, the external sheath may be pulled away, and the scaffold is then inserted into the targeted place through the external sheath.

Figure 2:
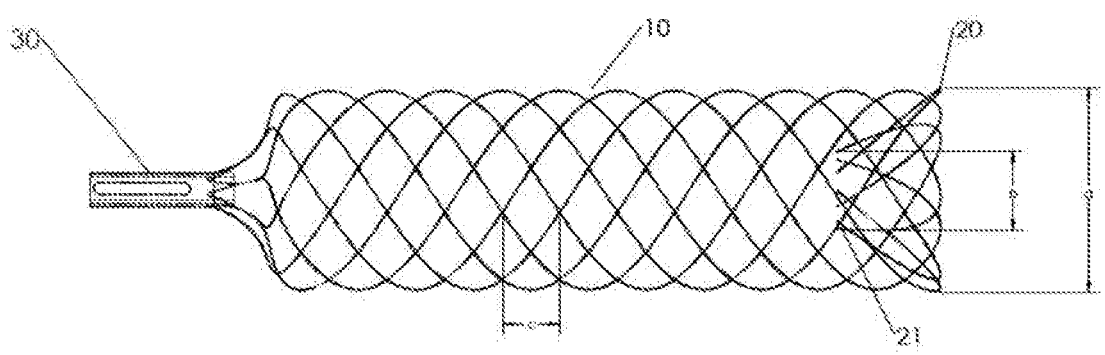
FIG. 2 is a schematic representation of a device or system in accordance with one embodiment of the present disclosure wherein the meshed scaffold is in open configuration.

FIG. 2 shows a medical device in accordance with one aspect of the present disclosure wherein the scaffold of the medical device is in an open configuration. Similar to what was described in FIG. 1, the difference is just that the scaffold 10 is in its open position wherein the inner elongate member 40 is pulled back into the lumen of the outer elongate member 30. The pull-back of the inner elongate member may be achieved through a handle (not shown) of the device by a user, or by ways/mechanisms known in the art.

When the scaffold 10 is in its open configuration, it has one or more of the following features in accordance with FIG. 2. The cage-like scaffold 10 may be made to be in any suitable shape, for example, a cylindrical structure. The cage-like scaffold 10 may be made to have any desirable cross-sectional shape and/or configuration, preferably substantially circular cross-section. The overall length and diameter of the cage-like scaffold may vary in accordance with its intended application. The scaffold 10 is composed of a plurality of wires that cross each other at points. The crossing of each other of the plurality of wires defines series of cells or spaces that may be configured to have any desirable pattern, configuration, and/or features that are suitable for entrapment of solid materials within a body lumen. The plurality of wires may be woven to form these cells or spaces. The wires are not physically connected into each other. That is the wires are not connected at crossing points. These cells or spaces may be of any suitable shape, size, and/or configuration. They may be in the shape of, for example, triangle, diamond, parallelogram, rectangle, square, or other polygons. Their diameter of these cells or spaces may be in a range of between about 0.05 inch and 0.15 inch (shown as distance "c" in FIG. 2).

The scaffold 10 of FIG. 2 is configured to have an inwardly everted tapering framework comprising a head portion 20 and a tail portion of 21. The head portion 20 starts from the distal end of the cage-like scaffold, and then tapers inwardly to form the tail portion 21 of the tapering framework. In an embodiment, the head portion may be in any suitable cross sectional shape such as a circular configuration. In an embodiment, the head portion may have a diameter of less than 0.40 inch but larger than 0.10 inch (shown as distance "a"). In an embodiment, the tail end may be in any suitable shape or configuration such as triangle, diamond, parallelogram, rectangle, square, other polygons, or other suitable geographic shapes. The diameter of the tail portion may be in the range of less than 0.20 inch but large than 0.02 inch (shown as distance "b"). The tail portion may be configured to have an even ending, meaning all the ends of the wires end on the same plane substantially perpendicular to the longitudinal axis of the cage-like scaffold. In alternative terms, the tail portion may be configured to have substantially the same wire length extending from the head portion. The tail portion may be configured to have an uneven ending, meaning all the ends of the wires do not end on the same plane. In alternative terms, the tail portion may be configured to have substantially different wire length extending from the head portion. The uneven ends may be symmetrical or non-symmetrical with respect to the longitudinal axis. In alternative terms, the tail portion may be configured to have uneven wire endings.

The inwardly everted tapering framework of the cage-like scaffold may be formed by taking the cylindrical piece of mesh and placing it in a form which forces it into the desired shape and heat treating it. This method is used to create other stone retrieval baskets made of similar materials. The tool can create a profile of any shape. The one displayed is round and symmetric, but it could be polygonal, asymmetric, or have wires of varying length to create a more effective trapping feature. The inwardly everted tapering framework does not require a separate or independent actuation mechanism to open and/or to close the tapering framework. Rather, it is configured to open and/or close in sync with the opening and/or the closing of the cage-like scaffold. That is the actuation of the cage-like scaffold will necessarily actuate the inwardly everted tapering framework, making the operation more convenient and more efficient.

Figure 3:
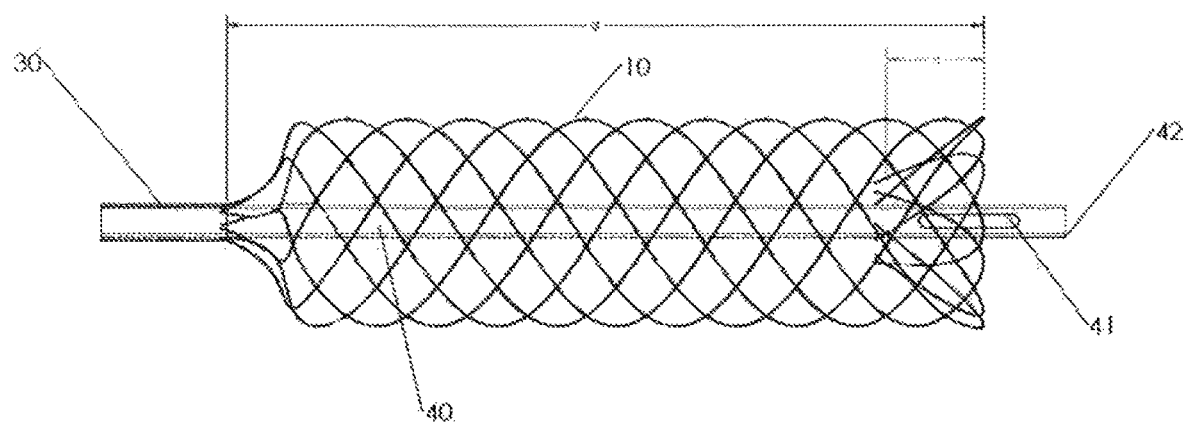
FIG. 3 is a schematic representation of a device or system in accordance with one embodiment of the present disclosure wherein the meshed scaffold is in open configuration, and the inner elongate member is extended out of the scaffold.

FIG. 3 shows a medical device in accordance with one aspect of the present disclosure wherein the scaffold of the medical device is in an open configuration and the inner elongate member is extended out of the scaffold 10. Similar to what was described in FIG. 2, the only difference is just that the inner elongate member 40 is configured to be extendable out of the scaffold 10 to facilitate to coax stones into the scaffold 10 by vacuum through the opening 41. The dimension and/or size and or location of the opening 41 may vary based on different purposes. For example, the opening may have a dimension of about 0.10 inch in length and about 0.02 inch in width and may be disposed at a distance of between about 0.10 inch and about 0.20 inch from the end of the inner elongate member. The inner elongate member may also be used to flush portion of the lumen if desirable. As shown in FIG. 3, the longitudinal length of the inwardly everted tapering framework may be between about 10% and about 25% that of the cage-like scaffold as measured from the proximal end to the distal end. Alternatively, the ration of "e" over "d" may be between about 10% and about 25% in accordance with FIG. 3.

Figure 4:
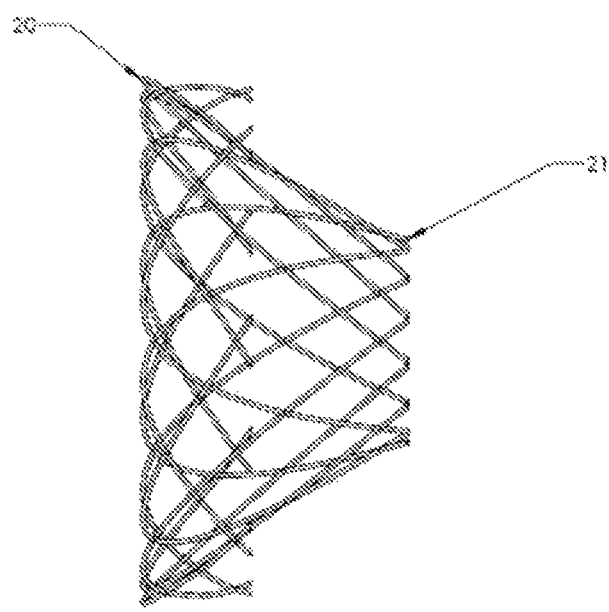
FIG. 4 is a more detailed illustration of the inwardly everted tapering framework in accordance with one embodiment of the present disclosure wherein the tail portion of the tapering framework has substantially equal ends.

FIG. 4 is a further illustration of one aspect of the inwardly everted tapering framework comprising the head portion 20 and the tail portion 21. In accordance with FIG. 4, the tail portion 21 all end substantially on the same plane substantially perpendicular to the longitudinal axis of the cage-like scaffold. In alternative terms, the tail portion is configured to have substantially the same wire length extending from the head portion. In further alternative terms, the tail portion is configured to have substantially even ending.

Figure 5:
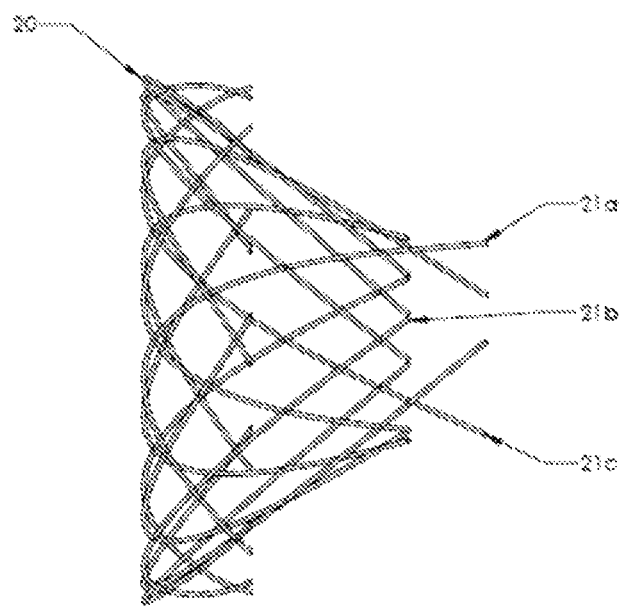
FIG. 5 is a more detailed illustration of the inwardly everted tapering framework in accordance with one embodiment of the present disclosure wherein the tail portion of the tapering framework has unequal ends.

FIG. 5 is an illustration of another aspect of the inwardly everted tapering framework comprising the head portion 20 and the tail portions 21a, 21b and 21c. In accordance with FIG. 5, the tail portions 21a, 21b, and 21c do not end on the same plane substantially perpendicular to the longitudinal axis of the cage-like scaffold. Rather, the tail portions 21a, 21b, and 21c are configured to have substantially different wire length extending from the head portion. In alternative terms, the tail portions 21a, 21b, and 21c ends unevenly, and these uneven ends are not symmetrical either.

Figure 6:
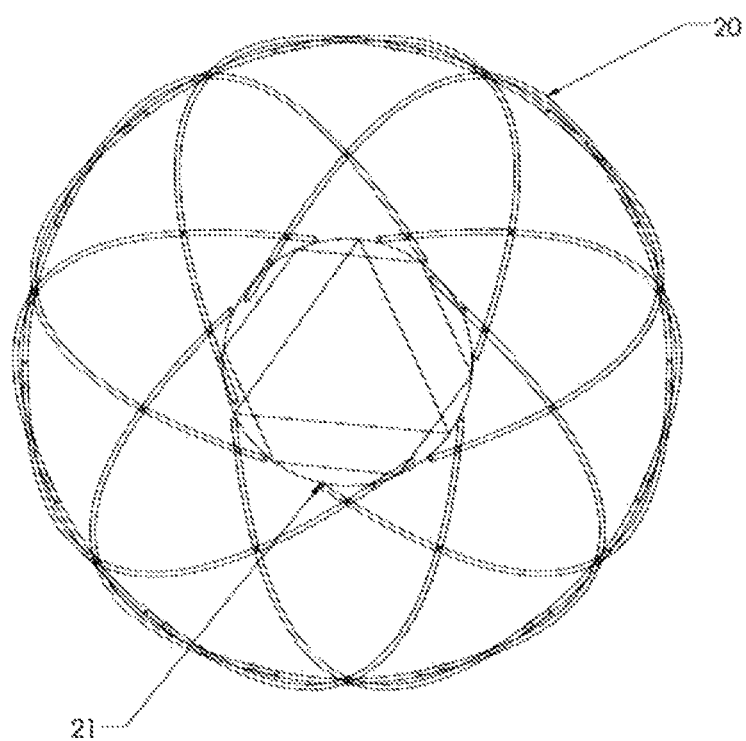
FIG. 6 is an end view from the head portion towards the tail portion of the inwardly everted tapering framework of the cage-like scaffold wherein the tail portion may be configured to end with different cross sectional geometries.

FIG. 6 is an end view from the head portion 20 towards the tail portion 21 of the inwardly everted tapering framework along the longitudinal axis. The cross section of the head portion 20 is substantially circular. But, it may be any other suitable geographic shapes. The cross section of the tail portion 21 may be configured to be in substantially circular, triangular, hexagonal as shown, but it may also be any suitable geographic shape.

The contents of all references, patents, pending patent applications and published patents, cited throughout this application are hereby expressly incorporated by reference.

While preferred embodiments of the present disclosure have been shown and described herein, it will be obvious to those skilled in the art that such embodiments are provided by way of example only. Numerous variations, changes, and substitutions will occur to those skilled in the art without departing from the disclosure. It should be understood that various alternatives to the embodiments of the disclosure described herein may be employed. It is intended that the following claims define the scope of the disclosure and that methods and structures within the scope of these claims and their equivalents be covered thereby.

What is claimed:

1. A medical device, comprising:
   an outer elongate member having a proximal end, a distal end, and a lumen extending therethrough;
   an inner elongate member having a proximal end portion, a distal end portion, and a lumen extending therethrough, the inner elongate member disposed within the lumen of the outer elongate member and configured to be axially movable relative to the outer elongate member; and
   an expandable cage-like scaffold, configured to he actuated between a substantially folded configuration and a substantially open configuration, having a substantially constant outer diameter over a length of the scaffold in the substantially open configuration, comprising:
   a plurality of wires that cross each other at points;

a proximal end secured to the distal end of the outer elongate member; and an unsecured distal end having an inwardly tapering framework including a central opening for passage of an object, wherein the inner elongate member is configured to be extendable through the expandable cage-like scaffold, wherein the inwardly tapering framework comprises at least one terminal wire end of the plurality of wires pointed proximally at a distal end of the expandable cage-like scaffold, wherein the inner elongate member is configured to provide suction against the object, via a distal opening of the inner elongate member, and urge the object proximally into the expandable cage-like scaffold for capture.

2. The medical device of claim 1, wherein the device further comprises a first actuator configured to actuate the expandable cage-like scaffold between the substantially folded configuration and the substantially open configuration.

3. The medical device of claim 2, wherein the device further comprises a second actuator configured to move the inner elongate member axially relative to the outer elongate member.

4. The medical device of claim 1, wherein he inwardly tapering framework comprises a head portion and a tail portion.

5. The medical device of claim 4, wherein the head portion has a substantially circular cross-section.

6. The medical device of claim 4, wherein the head portion has a diameter of between about 0.10 inch and about 0.40 inch.

7. The medical device of claim 4, wherein the tail portion has a substantially circular cross-section.

8. The medical device of claim 4, wherein the tail portion has a diameter of between about 0.05 inch and about 0.20 inch.

9. The medical device of claim 4, wherein each of the plurality of wires is configured to have different wire length, when measured from the head portion to the tail portion, forming a set of uneven ends.

10. The medical device of claim 9, wherein each of the set of uneven ends are asymmetrical with respect to a longitudinal axis.

11. The medical device of claim 1, wherein the inner elongate member is configured to extend beyond the distal end of the expandable cage-like scaffold.

12. The medical device of claim 1, wherein the inner elongate member is flexible along at least a portion of its length.

13. The medical device of claim 1, wherein the expandable cage-like scaffold is configured for self-expansion.

14. The medical device of claim 1, wherein the expandable cage-like scaffold is configured to have a cylindrical shape.

15. The medical device of claim 1, wherein the plurality of wires are woven together and not physically connected at crossing points.

16. A method, comprising:

advancing the medical device of claim 1 to a treatment location;

opening the expandable cage-like scaffold;

capturing materials at the treatment location; and.

removing the medical device from the treatment location.

17. The method of claim 16, further comprising actuating a first actuator to move the expandable cage-like scaffold between the substantially folded configuration and the substantially open configuration.

18. The method of claim 17, further comprising actuating a second actuator to move the inner elongate member axially relative to the outer elongate member.

19. The medical device of claim 1, wherein the inwardly everted tapering framework is formed by placing a mesh in a form and heat treating the mesh.

20. A medical device, comprising:

an outer elongate member having a proximal end, a distal end, and a lumen extending therethrough;

an inner elongate member having a proximal end portion, a distal end portion, and a lumen extending therethrough, the inner elongate member disposed within the lumen of the outer elongate member; and an expandable cage-like scaffold, configured to be actuated between a substantially folded configuration and a substantially open configuration, having a substantially constant outer diameter over a length of the scaffold in the substantially open configuration, comprising:

a plurality of wires that cross each other at points;

a proximal end secured to the distal end of the outer elongate member; and an unsecured distal end having an inwardly tapering framework including a central opening for passage of an object, wherein the inner elongate member is configured to be longitudinally extendable and retractable through a mid-section of the expandable cage-like scaffold, wherein the inner elongate member is configured to provide suction against the object, via a distal opening of the inner elongate member, and urge the object proximally into the expandable cage-like scaffold for capture.

21. The medical device of claim 20, wherein the inwardly tapering framework comprises at least one terminal wire end of the plurality of wires pointed proximally at a distal end of the expandable cage-like scaffold.

* * * * *

UNITED STATES PATENT AND TRADEMARK OFFICE
CERTIFICATE OF CORRECTION

PATENT NO. : 10,722,256 B2  
APPLICATION NO. : 14/867055  
DATED : July 28, 2020  
INVENTOR(S) : Mansfield et al.

Page 1 of 1

It is certified that error appears in the above-identified patent and that said Letters Patent is hereby corrected as shown below:

On the Title Page

Item (71), in "Applicant", in Column 1, Line 1, delete "GYRUS ACMI, INC.," and insert --GYRUS ACMI, INC., d/b/a Olympus Surgical Technologies America,-- therefor Item (73), in "Assignee", in Column 1, Line 1, delete "Gyrus Acmi, Inc.," and insert --Gyrus Acmi, Inc. DBA Olympus Surgical Technologies America,-- therefor In the Claims In Column 12, Line 62, in Claim 1, delete "he" and insert --be-- therefor In Column 13, Line 26, in Claim 4, delete "he" and insert --the-- therefor In Column 14, Line 11, in Claim 16, delete "and." and insert --and-- therefor Signed and Sealed this  
Twentieth Day of October, 2020

Andrei Iancu  
*Director of the United States Patent and Trademark Office*